(12) United States Patent
Nanba et al.

(10) Patent No.: US 6,756,229 B1
(45) Date of Patent: Jun. 29, 2004

(54) HUMAN CELL LINE SHOWING STABLE EXPRESSION OF CYTOCHROMES P450

(75) Inventors: Masayoshi Nanba, 400-1, Syuku, Okayama-shi, Okayama (JP), 700-0001; Satoru Asahi, Toyonaka (JP); Sumie Yoshitomi, Osaka (JP); Keiko Ikemoto, Takarazuka (JP)

(73) Assignees: Takeda Chemical Industries, Ltd., Osaka (JP); Masayoshi Nanba, Okayama (JP)

( * ) Notice: Subject to any disclaimer, the term of this patent is extended or adjusted under 35 U.S.C. 154(b) by 0 days.

(21) Appl. No.: 10/009,158

(22) PCT Filed: Apr. 27, 2000

(86) PCT No.: PCT/JP00/02763

§ 371 (c)(1),
(2), (4) Date: Oct. 25, 2001

(87) PCT Pub. No.: WO00/65031

PCT Pub. Date: Nov. 2, 2000

(30) Foreign Application Priority Data

Apr. 27, 1999 (JP) ............................................ 11-120747

(51) Int. Cl.[7] ............................ C12N 5/08; C12N 9/02; C07H 21/04
(52) U.S. Cl. ........................ 435/370; 435/189; 536/23.2
(58) Field of Search ................................ 435/370, 189; 536/23.2

(56) References Cited

FOREIGN PATENT DOCUMENTS

| | | | |
|---|---|---|---|
| WO | WO 94/26905 | 11/1994 | ............ C12N/15/53 |
| WO | WO 97/10344 | 3/1997 | ............ C12N/15/81 |

OTHER PUBLICATIONS

Waxman DJ, Lapenson DP, Aoyama T, Gelboin HV, Gonzalez FJ, Korzekwa K. Steroid hormone hydroxylase specificities of eleven cDNA–expressed human cytochrome P450s. Arch Biochem Biophys. Oct. 1991;290(1):160–6.*
Miyazaki et al., "Hepatocellular Carcinomas," Atlas of Human Tumor Cell Lines, pp. 185–212 (1994).
The Journal of Pharmacology and Experimental Therapeutics (1995), vol. 273, No. 3, pp. 1497–1505; Dai et.al.
The Journal of Biological Chemistry (1996), vol. 271. No. 39, pp. 23914–23919; Wu.D. et al.
Xenobiotica (1998), vol. 28, No. 12, pp. 1129–1165; Smith G et al.
Cancer Research (1996), vol. 56. No. 2, pp. 299–304; deGroene En. et al.
Nature vol. 282, 615–616, 1979; Aden D.P. et al.
Methods in Enzymology, vol. 206, pp. 85–92, 1991; Gonzalez FJ et al.
Biochemistry, 32, 6928–6937, 1993. Dai Y et al.

* cited by examiner

*Primary Examiner*—Rebecca E. Prouty
*Assistant Examiner*—Sheridan Swope
(74) *Attorney, Agent, or Firm*—David G. Conlin; Kathryn A. Piffat; Edwards & Angell, LLP

(57) ABSTRACT

This invention relates to cell lines that are obtained using cultured cell lines derived from human liver as a host and that stably express a number of human cytochromes P450. The human liver-derived cultured cell lines of the present invention are useful in, for example, analyzing an enzyme participating in the metabolism of xenobiotics or endogenous substrates, because of their stable expression of human cytochromes P450 CYP1A1, 1A2, 2A6, 2B6, 2C8, 2C9, 2C9, 2D6, and 3A4.

1 Claim, 7 Drawing Sheets

HUMAN CELL LINE SHOWING STABLE EXPRESSION OF CYTOCHROMES P450

This application is a U.S. 371 filing of PCT/JP00/02763, filed Apr. 27, 2000 and claims the benefit of priority to Japan 120747/1999, filed Apr. 27, 1999.

FIELD OF THE INVENTION

This invention relates to the following features.

1. A cell line derived from human hepatic carcinoma capable of stably expressing human cytochromes P450.

2. (1) A method for analyzing an enzyme participating in the metabolism of a xenobiotic and/or an endogenous substrate, (2) a method for analyzing a metabolic pathway of a xenobiotic and/or an endogenous substrate, (3) a method for analyzing a chemical structure of the metabolite of a xenobiotic and/or an endogenous substrate, (4) a method for preparing the metabolite of a xenobiotic and/or an endogenous substrate, (5) a method for analyzing inhibition of the metabolizing enzyme for a xenobiotic and/or an endogenous substrate, (6) a method for analyzing an accelerated activity of the metabolizing enzyme for a xenobiotic and/or an endogenous substrate, (7) a method for analyzing expression of cytotoxicity by the metabolism of a xenobiotic and/or an endogenous substrate, (8) a method for analyzing expression of genotoxicity by the metabolism of a xenobiotic and/or an endogenous substrate, (9) a method for analyzing expression of carcinogenicity by the metabolism of a xenobiotic and/or endogenous substrate, (10) a method for analyzing mutagenicity by the metabolism of a xenobiotic and/or an endogenous substrate, (11) a method for analyzing expression of hepatotoxicity by the metabolism of a xenobiotic and/or an endogenous substrate, and (12) a method for analyzing a xenobiotic and/or an endogenous substrate that acts on the liver, each method comprising use of the cell line according to (1).

3. (1) A method for screening a substance capable of inhibiting a xenobiotic and/or an endogenous substrate, (2) a method for screening a substance capable of accelerating the activity of a metabolizing enzyme for a xenobiotic and/or an endogenous substrate, (3) a method for screening a substance capable of expressing cytotoxicity by the metabolism of a xenobiotic and/or an endogenous substrate, (4) a method for screening a substance capable of expressing genotoxicity by the metabolism of a xenobiotic and/or an endogenous substrate, (5) a method for screening a substance capable of expressing carcinogenicity by the metabolism of a xenobiotic and/or an endogenous substrate, (6) a method for screening a substance capable of expressing mutagenicity by the metabolism of a xenobiotic and/or an endogenous substrate, (7) a method for screening a substance capable of expressing hepatotoxicity by the metabolism of a xenobiotic and/or an endogenous substrate, (8) a method for screening a xenobiotic and/or an endogenous substrate which acts on the liver, and (9) a method for screening a substance capable of acquiring a new physiological activity or increasing or decreasing the inherent physiological activity, through the metabolism of a xenobiotic and/or an endogenous substrate, each method comprising use of the cell line according to 1.

4. A compound or its salt obtainable using the screening method according to 3.

BACKGROUND ART

Hepatocytes are known to have a great many physiological functions, all of which play a very important function in terms of the metabolism of xenobiotics and/or endogenous substrates such as drugs, food additives, environmental pollutants, industrial chemicals and the like. At the same time, the function of metabolizing xenobiotics and/or endogenous substrates might lead to inducing the inhibition of metabolizing enzymes for xenobiotics and/or endogenous substrates by xenobiotics and/or endogenous substrates, to accelerate the activity of metabolizing enzymes for xenobiotics and/or endogenous substrates, to express cytotoxicity by the metabolism of xenobiotics and/or endogenous substrates, to express genotoxicity by the metabolism of xenobiotics and/or endogenous substrates, to express carcinogenicity by the metabolism of xenobiotics and/or endogenous substrates, to express mutagenicity by the metabolism of xenobiotics and/or endogenous substrates, to express hepatotoxicity by the metabolism of xenobiotics and/or endogenous substrates, and so on. For these reasons, the function of xenobiotics and/or endogenous substrates has been widely studied. It is known that many enzymes are associated with the metabolism of xenobiotics and/or endogenous substrates referred to herein. Examples of such enzymes include UDP-glucuronosyltransferase, sulfotransferase, glutathione transferase, epoxy hydratase, N-acetyltransferase, flavin monooxygenase and cytochromes P450. Also, the presence of a cytochrome P450 reductase is crucial for expressing the enzymatic function of cytochromes P450. Of an array of these enzymes, cytochromes P450 play the most important role in the metabolism of xenobiotics and/or endogenous substrates. The term cytochromes P450 collectively refers to a class of enzymes including a great many molecular species. In the metabolism of xenobiotics and/or endogenous substrates in human liver, ten (10) species of CYP1A1, CYP1A2, CYP2A6, CYP2B6, CYP2C8, CYP2C9, CYP2C19, CYP2D6, CYP2E1 and CYP3A4 are considered important. Also, these enzymes, which are distributed in human liver, are functionally different depending on species and hence, human-derived liver specimens are unable to be used as a stable test system. On the other hand, such a metabolic function of the liver involves a very strong specificity, i.e., differences in nature, depending on species, which makes it difficult to predict such diverse metabolic functions of human liver from experimental animals, e.g., rats. However, it is practically impossible to analyze these functions of interest in humans. For these reasons, human-derived cultured hepatocytes are considered useful not only in examining the function of human liver in a rapid, inexpensive, safe and accurate way provided in place of experimental animals, but also in producing a so-called artificial liver as a functional substitute for human liver. However, it is impossible to subculture normal human hepatocytes separated from tissues in vivo. Cells that can be established as a cell line often lack the differentiation capability possessed inherently and in most cases, do not exactly reflect the function of tissues to which the cell line originally belongs. A family of enzymes that metabolize xenobiotics and/or endogenous substrates especially in liver cells, among others, the family of cytochromes P450 molecular species loses its activity in an extremely short period of time in primary culture; any cell line that fully retains the property has not been found so far (J. Dich et al., Hepatology, 8, 39–45 (1988)). Thus, in light of the foregoing, there is an extensive need for hepatocytes that can retain the capability of metabolizing xenobiotics and/or endogenous substrates and can be incubated.

To date, however, no cultured cell line has been obtained as retaining the function associated with the metabolism of xenobiotics and/or endogenous substrates as in the liver.

Particularly because the activity of cytochromes P450 is widely recognized to be rapidly lost in cultured cells, it has been hitherto attempted to stably express cytochromes P450 in the established cultured cells and by this, take over the metabolizing function of liver (M. Sawada et al., Mutation Research, 411, 19–43 (1998)). However, as stated above, the cell line for expression of cytochromes P450 should indispensably be derived from human liver cells. In addition, the activity of NADPH cytochromes P450 reductase is required for expressing the activity of cytochromes P450, requiring further expression of many more enzymes. Therefore, stable and safe reproduction of the metabolizing function in human liver should be in human-derived cultured hepatocytes that retain the activity of enzymes participating in the metabolism of cytochromes P450 as well as various other metabolisms.

As examples of the expression of cytochromes P450 in cells retaining the activity of various enzymes participating in metabolism, there are cases in which P450 was expressed in HepG2 cells using vaccinia virus (Methods in Enzymology, T. Aoyama et al. in Methods in Enzymology, 260, 85–92, edited by M. R. Waterman, Academic Press, 1991) and in which CYP2E1 was expressed in HepG2 cells (Y. Dai et al., Biochemistry, 32, 6928–6937, 1993). In the former case, careful handling is required, which is an obstacle to practical application. The latter was attempted for CYP2E1 alone but so far has not been attempted for many other species of cytochromes P450 present in the liver. Accordingly, if a cultured cell line that can retain the activity of a family of enzymes participating in the metabolism of xenobiotics and/or endogenous substrates in the liver could be obtained, this would enable a practitioner to (1) analyze an enzyme participating in the metabolism of xenobiotics and/or endogenous substrates, (2) analyze a metabolic pathway of xenobiotics and/or endogenous substrates, (3) analyze a chemical structure of the metabolite of xenobiotics and/or endogenous substrates, (4) prepare the metabolite of xenobiotics and/or endogenous substrates, (5) analyze inhibition of the metabolizing enzyme for xenobiotics and/or endogenous substrates, (6) analyze an accelerated activity of the metabolizing enzyme for xenobiotics and/or endogenous substrates, (7) analyze expression of cytotoxicity by the metabolism of xenobiotics and/or endogenous substrates, (8) analyze expression of genotoxicity by the metabolism of xenobiotics and/or endogenous substrates, (9) analyze expression of carcinogenicity by the metabolism of xenobiotics and/or endogenous substrates, (10) analyze mutagenicity by the metabolism of xenobiotics and/or endogenous substrates, (11) analyze expression of hepatotoxicity by the metabolism of xenobiotics and/or endogenous substrates, and (12) analyze xenobiotics and/or endogenous substrates that act on the liver. Furthermore, this would enable a practitioner to (1) screen a substance capable of inhibiting xenobiotics and/or endogenous substrates, (2) screen a substance capable of accelerating the activity of metabolizing enzymes for xenobiotics and/or endogenous substrates, (3) screen a substance capable of expressing cytotoxicity by the metabolism of xenobiotics and/or endogenous substrates, (4) screen a substance capable of expressing genotoxicity by the metabolism of xenobiotics and/or endogenous substrates, (5) screen a substance capable of expressing carcinogenicity by the metabolism of xenobiotics and/or endogenous substrates, (6) screen a substance capable of expressing mutagenicity by the metabolism of xenobiotics and/or endogenous substrates, (7) screen a substance capable of expressing hepatotoxicity by the metabolism of xenobiotics and/or endogenous substrates, (8) screen xenobiotics and/or endogenous substrates which act on the liver, and (9) screen a substance capable of acquiring a new physiological activity or increasing or decreasing the inherent physiological activity, through the metabolism of xenobiotics and/or endogenous substrates. Thus, specific compounds or salts thereof, etc. can be obtained using the method for analysis and/or the method for screening above.

DISCLOSURE OF THE INVENTION

An object of this invention is to provide a cultured cell line derived from human liver, thereby to separate and produce the cell line that can stably express human cytochromes P450 CYP1A1, CYP1A2, CYP2A6, CYP2B6, CYP2C8, CYP2C9, CYP2C19, CYP2D6, CYP2E1 and CYP3A4.

These cells enable a practitioner of the invention to (1) analyze an enzyme participating in the metabolism of xenobiotics and/or endogenous substrates, (2) analyze a metabolic pathway of xenobiotics and/or endogenous substrates, (3) analyze a chemical structure of the metabolite of xenobiotics and/or endogenous substrates, (4) prepare the metabolite of xenobiotics and/or endogenous substrates, (5) analyze inhibition of the metabolizing enzyme for xenobiotics and/or endogenous substrates, (6) analyze an accelerated activity of the metabolizing enzyme for xenobiotics and/or endogenous substrates, (7) analyze expression of cytotoxicity by the metabolism of xenobiotics and/or endogenous substrates, (8) analyze expression of genotoxicity by the metabolism of xenobiotics and/or endogenous substrates, (9) analyze expression of carcinogenicity by the metabolism of xenobiotics and/or endogenous substrates, (10) analyze mutagenicity by the metabolism of xenobiotics and/or endogenous substrates, (11) analyze the expression of hepatotoxicity by the metabolism of xenobiotics and/or endogenous substrates, and (12) analyze xenobiotics and/or endogenous substrates that act on the liver. The cells further enable a practitioner of the invention to (1) screen a substance capable of inhibiting xenobiotics and/or endogenous substrates, (2) screen a substance capable of accelerating the activity of metabolizing enzymes for xenobiotics and/or endogenous substrates, (3) screen a substance capable of expressing cytotoxicity by the metabolism of xenobiotics and/or endogenous substrates, (4) screen a substance capable of expressing genotoxicity by the metabolism of xenobiotics and/or endogenous substrates, (5) screen a substance capable of expressing carcinogenicity by the metabolism of xenobiotics and/or endogenous substrates, (6) screen a substance capable of expressing mutagenicity by the metabolism of xenobiotics and/or endogenous substrates, (7) screen a substance capable of expressing hepatotoxicity by the metabolism of xenobiotics and/or endogenous substrates, (8) screen xenobiotics and/or endogenous substrates which act on the liver, and (9) screen a substance capable of acquiring a new physiological activity or increasing or decreasing the inherent physiological activity, through the metabolism of xenobiotics and/or endogenous substrates. Thus, particular compounds or salts thereof, etc. can be obtained, using the method for analysis and/or the method for screening.

In view of the foregoing problems, the present inventors have made extensive studies. As a result, they have established stable transformants capable of stably expressing cytochromes P450 in a human hepatocarcinoma-derived (or hepatic carcinoma-derived) cell line with an enhanced activity for participation in the metabolism of xenobiotics and/or endogenous substrates. The following further studies have resulted in accomplishing this invention.

That is, the present invention relates to the following features.

(1) A cell line derived from human hepatic carcinoma capable of stably expressing human cytochromes P450.

(2) The cell line according to (1), wherein human cytochromes P450 are capable of stably expressing CYP1A1, CYP1A2, CYP2A6, CYP2B6, CYP2C8, CYP2C9, CYP2C19, CYP2D6, CYP2E1 or CYP3A4.

(3) The cultured cell line according to (1), wherein the human hepatic carcinoma cell is HepG2.

(4) The cell line according to (1), which is Hepc/1A1.4, Hepc/1A2.9, Hepc/2B6.68, Hepc/2C8.46, Hepc/2C9.1, Hepc/2C19.12, Hepc/2D6.39, Hepc/2E1.3–8 or Hepc/3A4.5.

(5) A method for analyzing (a) an enzyme participating in the metabolism of a xenobiotic and/or an endogenous substrate, (b) a metabolic pathway of a xenobiotic and/or an endogenous substrate, (c) a chemical structure of the metabolite of a xenobiotic and/or an endogenous substrate, (d) inhibition of the metabolizing enzyme for a xenobiotic and/or an endogenous substrate, (e) an accelerated activity of the metabolizing enzyme for a xenobiotic and/or an endogenous substrate. (f) cytotoxicity by the metabolism of a xenobiotic and/or an endogenous substrate. (g) genotoxicity by the metabolism of a xenobiotic and/or an endogenous substrate, (h) carcinogenicity by the metabolism of a xenobiotic and/or endogenous substrate, (i) mutagenicity by the metabolism of a xenobiotic and/or an endogenous substrate, (j) hepatotoxicity by the metabolism of a xenobiotic and/or an endogenous substrate, or (k) a xenobiotic and/or an endogenous substrate that acts on the liver.

(6) A method for preparing the metabolite of a xenobiotic and/or an endogenous substrate, which comprises using the cell line according to (1).

(7) A method for screening a substance which comprises using the cell line according to (1), wherein the substance is (a) a substance capable of inhibiting a xenobiotic and/or an endogenous substrate, (b) a substance capable of accelerating an activity of the metabolizing enzyme for a xenobiotic and/or an endogenous substrate, (c) a substance capable of expressing cytotoxicity by the metabolism of a xenobiotic and/or an endogenous substrate, (d) a substance capable of expressing genotoxicity by the metabolism of a xenobiotic and/or an endogenous substrate, (e) a substance capable of expressing carcinogenicity by the metabolism of a xenobiotic and/or an endogenous substrate, (f) a substance capable of expressing mutagenicity by the metabolism of a xenobiotic and/or an endogenous substrate, (g) a substance capable of expressing hepatotoxicity by the metabolism of a xenobiotic and/or an endogenous substrate, (h) a xenobiotic and/or an endogenous substrate which acts on the liver, or (i) a substance capable of acquiring a new physiological activity or increasing or decreasing the inherent physiological activity, through the metabolism of a xenobiotic and/or an endogenous substrate.

(8) A compound or its salt which is obtainable using the method according to (7).

(9) A pharmaceutical composition comprising the compound or its salt according to (8).

(10) A method for analysis which comprises using at least two cultured cell lines derived from human liver capable of stably expressing at least one of CYP1A1, CYP1A2, CYP2A6, CYP2B6, CYP2C8, CYP2C9, CYP2C19, CYP2D6, CYP2E1 and CYP3A4, said analysis being for (a) an enzyme that participates in the metabolism of a xenobiotic and/or an endogenous substrate, (b) a metabolic pathway of a xenobiotic and/or an endogenous substrate, (c) a chemical structure of the metabolite of a xenobiotic and/or an endogenous substrate, (d) inhibition of the metabolizing enzyme for a xenobiotic and/or an endogenous substrate, (e) an accelerated activity of the metabolizing enzyme for a xenobiotic and/or an endogenous substrate, (f) cytotoxicity by the metabolism of a xenobiotic and/or an endogenous substrate, (g) genotoxicity by the metabolism of a xenobiotic and/or an endogenous substrate, (h) carcinogenicity by the metabolism of a xenobiotic and/or endogenous substrate, (i) mutagenicity by the metabolism of a xenobiotic and/or an endogenous substrate, (j) hepatotoxicity by the metabolism of a xenobiotic and/or an endogenous substrate, or (k) a xenobiotic and/or an endogenous substrate that acts on the liver.

(11) A method for preparation of the metabolite of a xenobiotic and/or an endogenous substrate, which comprises using at least two cultured cell lines from human liver capable of stably expressing at least one of CYP1A1, CYP1A2, CYP2A6, CYP2B6, CYP2C8, CYP2C9, CYP2C19, CYP2D6, CYP2E1 and CYP3A4.

(12) A method for screening a substance which comprises using at least two cultured cell lines from human liver capable of stably expressing at least one of CYP1A1, CYP1A2, CYP2A6, CYP2B6, CYP2C8, CYP2C9, CYP2C19, CYP2D6, CYP2E1 and CYP3A4, said substance being (a) a substance capable of inhibiting the metabolizing enzyme for a xenobiotic and/or an endogenous substrate, (b) a substance capable of accelerating an activity of the metabolizing enzyme for a xenobiotic and/or an endogenous substrate, (c) a substance capable of expressing cytotoxicity by the metabolism of a xenobiotic and/or an endogenous substrate, (d) a substance capable of expressing genotoxicity by the metabolism of a xenobiotic and/or an endogenous substrate, (e) a substance capable of expressing carcinogenicity by the metabolism of a xenobiotic and/or an endogenous substrate, (f) a substance capable of expressing mutagenicity by the metabolism of a xenobiotic and/or an endogenous substrate, (g) a substance capable of expressing hepatotoxicity by the metabolism of a xenobiotic and/or an endogenous substrate, (h) a xenobiotic and/or an endogenous substrate which acts on the liver, or (i) a substance capable of acquiring a new physiological activity or increasing or decreasing the inherent physiological activity, through the metabolism of a xenobiotic and/or an endogenous substrate.

(13) A compound or a salt thereof, which is obtainable using the method according to (12).

(14) A pharmaceutical compound comprising a compound or a salt thereof according to (13).

BEST MODE OF EMBODIMENT OF THE INVENTION

Figure 1:
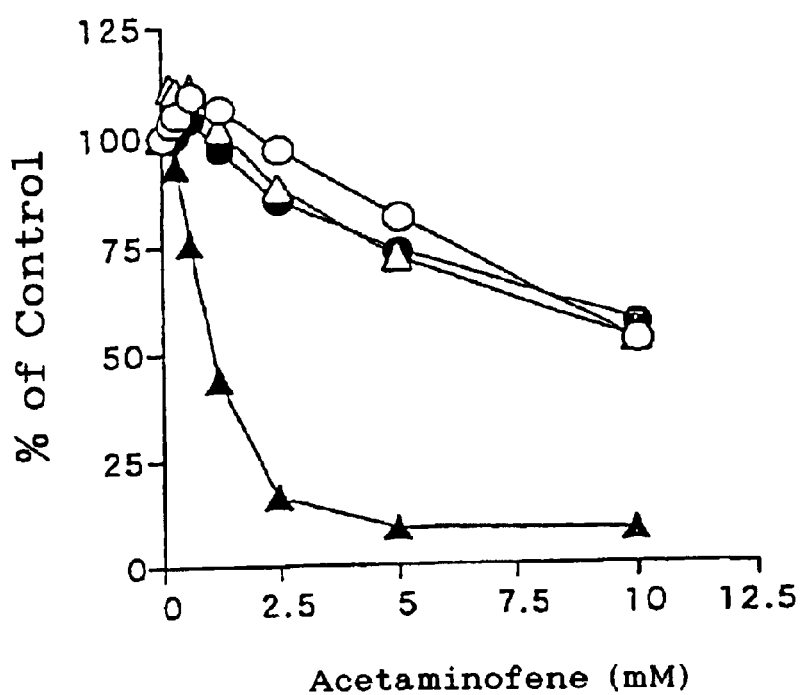
FIG. 1 shows the results by the MTT assay method relating to expression of cytotoxicity of acetaminophen shown in EXAMPLE 4, wherein symbols -○-, -△-, -●- and -▲- denote HepG2, Hepc/2E1.3–8, HepG2+100 μM BSO and Hepc/2E1.3–8+100 μM BSO, respectively.

Throughout the specification, the term "xenobiotics or foreign matters in vivo" collectively refers to, e.g., medicaments, food additives, environmental pollutants, chemicals in general, etc. and the term "endogenous substrates" refers to all substances present in vivo. For the metabolism of xenobiotics, among others, medicaments or drugs as the main component, drug metabolism is preferably used.

The human hepatic carcinoma cells used can be collected by separating a human hepatic carcinoma-derived cultured cell line (preferably HepG2) from human hepatic carcinoma. Genes that encode various species of cytochromes P450 separately isolated are stably expressed in the human hepatic carcinoma cells.

In order to stably express DNA fragments encoding cytochromes P450, first, DNA fragments encoding, e.g., individual cytochromes P450 are obtained and placed under control of a foreign promoter for expression. The base sequences of DNA fragments encoding cytochromes P450 are available from public database. Based on the base sequences, a cytochromes P450-encoding DNA fragment can be isolated by publicly known methods including PCR, hybridization screening, etc. The DNA fragment thus obtained is inserted into a vector which produces transformants capable of stably expressing a foreign gene in a cultured mammalian cell, whereby a vector for transformation is produced. The resulting vector is transfected into hepatic carcinoma cells by publicly known methods. Transformants are selected by examining the enzyme activity induced by the expression of cytochromes P450 transformed therein, in order to select excellent clones. In addition, clones obtained can be confirmed with stability of their properties through repeated frozen storage.

Examples of the foreign promoter include SRα promoter, SV40 promoter, LTR promoter, CMV promoter and HSV-TK promoter.

The term "stably expressing human cytochromes P450" is used to mean that the expression of human cytochromes P450 is not transient and specifically, the activity of cytochromes P450 is not lost when cells are cultured (subcultured). The cells capable of expressing human cytochromes P450 are preferably cells in which not only cytochromes P450 but also enzymes associated with various aspects of metabolism (specifically, UDP-glucuronosyltransferase, sulfotransferase, glutathione transferase, epoxy hydratase, N-acetyltransferase, flavin monooxygenase, etc.) are capable of functioning.

Examples of the cytochromes P450 molecular species which participate in the metabolism of xenobiotics and/or endogenous substrates in liver include CYP1A1, CYP1A2, CYP2A6, CYP2B6, CYP2C8, CYP2C9, CYP2C19, CYP2D6, CYP2E1 and CYP3A4. These enzymes not only catalyze the metabolism of xenobiotics and/or endogenous substrates but also induce, depending upon properties of their metabolites, the inhibition of metabolizing enzymes for xenobiotics and/or endogenous substrates, the acceleration of the activity of metabolizing enzymes for xenobiotics and/or endogenous substrates, the expression of cytotoxicity by the metabolism of xenobiotics and/or endogenous substrates, the expression of genotoxicity by the metabolism of xenobiotics and/or endogenous substrates, the expression of carcinogenicity by the metabolism of xenobiotics and/or endogenous substrates, the expression of mutagenicity by the metabolism of xenobiotics and/or endogenous substrates, the expression of hepatotoxicity by the metabolism of xenobiotics and/or endogenous substrates, and so on. However, these functions associated with the metabolism of xenobiotics and/or endogenous substrates are not only catalyzed by cytochromes P450 alone but are dependent on concerted actions with various enzymes such as UDP-glucuronosyltransferase, sulfotransferase, glutathione transferase, epoxy hydratase, N-acetyltransferase, flavin monooxygenase and cytochromes P450 reductase.

For reproducing the function of the liver by expressing cytochromes P450, the cells should thus be those capable of functioning at least, human-derived UDP-glucuronosyltransferase, sulfotransferase, glutathione transferase, epoxy hydratase, N-acetyltransferase or flavin monooxygenase in the cells. One of such cells is cultured cell HepG2 originating from human hepatic carcinoma. The HepG2 cell is known to be capable of functioning UDP-glucuronosyltransferase, sulfotransferase, glutathione transferase, epoxy hydratase, N-acetyltransferase, flavin monooxygenase and NADPH P450 reductase function in HepG2 (J. Rueffet al., Mutation Research, 353, 151–176 (1996). In light of the foregoing, the present inventors have succeeded in stably expressing cytochromes P450 in HepG2 in order to reproduce the function of human liver in a rapid, inexpensive, safe and accurate fashion.

In particular, preferred embodiments include Hepc/3A4.5, Hepc/2E1.3–8, Hepc/2C9.1, Hepc/2C8.46, Hepc/1A2.9, Hepc/1A1.4, Hepc/2B6.68, Hepc/2D6.39, Hepc/2A6L.9, Hepc/2C19.12, etc.

Hepc/3A4.5, Hepc/2E1.3–8, Hepc/2C9.1, Hepc/2C8.46, Hepc/1A2.9, Hepc/1A1.4, Hepc/2B6.68, Hepc/2D6.39, Hepc/2A6L.9 and Hepc/2C19.12 are highly active cells obtained by the expression of CYP3A4, CYP2E1, CYP2C9, CYP2C8, CYP1A2, CYP1A1, CYP2B6, CYP2D6, CYP2A6 and CYP2C19, respectively.

The present invention further relates to a method, which comprises using the aforesaid human hepatic carcinoma-derived cultured cell line capable of stably expressing human cytochromes P450, including (a) a method for analyzing an enzyme participating in the metabolism of a xenobiotic and/or an endogenous substrate, (b) a method for analyzing a metabolic pathway of a xenobiotic and/or an endogenous substrate, (c) a method for analyzing a chemical structure of the metabolite of a xenobiotic and/or an endogenous substrate, (d) a method for preparing the metabolite of a xenobiotic and/or an endogenous substrate, (e) a method for analyzing inhibition of the metabolizing enzyme for a xenobiotic and/or an endogenous substrate, (f) a method for analyzing an accelerated activity of the metabolizing enzyme for a xenobiotic and/or an endogenous substrate, (g) a method for analyzing expression of cytotoxicity by the metabolism of a xenobiotic and/or an endogenous substrate, (h) a method for analyzing expression of genotoxicity by the metabolism of a xenobiotic and/or an endogenous substrate, (i) a method for analyzing expression of carcinogenicity by the metabolism of a xenobiotic and/or endogenous substrate, (j) a method for analyzing mutagenicity by the metabolism of a xenobiotic and/or an endogenous substrate, (k) a method for analyzing expression of hepatotoxicity by the metabolism of a xenobiotic and/or an endogenous substrate, and (l) a method for analyzing a xenobiotic and/or an endogenous substrate that acts on the liver.

The respective methods described in (a) through (l) are described below.

(a) Method for Analyzing an Enzyme Participating in the Metabolism of Xenobiotics and/or Endogenous Substrates:

By analyzing a change in the structure of xenobiotics and/or endogenous substrates through exposure of a test specimen, e.g., to the human hepatic carcinoma-derived cultured cell line capable of stably expressing cytochromes P450, enzymes that participate in the metabolism of xenobiotics and/or endogenous substrates can be analyzed (J. L. Napoli et al., Methods in Enzymology, vol. 206, pp. 491–501, Ed. by M. R. Waterman et al., Academic Press, 1991; H. K. Kroemer et al., Methods in Enzymology, vol. 272, pp. 99–108, Ed. by M. R. Waterman et al., Academic Press, 1996). Specific examples include identification of an enzyme participating the metabolism of xenobiotics and/or endogenous substrates by analyzing a change in the structure of xenobiotics and/or endogenous substrates upon exposure of a test specimen to the human hepatic carcinoma-derived cultured cell line capable of stably expressing cytochromes P450. Other specific examples include analysis of the mechanism in an enzymatic reaction by analyzing a change in the structure of xenobiotics and/or endogenous substrates upon exposure of a test specimen of interest to the cell, and analysis of substrate specificity.

Examples of the test specimen to be tested include a peptide, a protein, a non-peptidic compound, a synthetic compound, a fermentation product, a cell extract, a plant extract, an animal tissue extract, plasma, etc. These substances may be either novel or publicly known ones.

(b) Method for Analyzing a Metabolic Pathway of Xenobiotics and/or Endogenous Substrates:

By analyzing a change in the structure of xenobiotics and/or endogenous substrates through exposure of a test specimen, e.g., to the human hepatic carcinoma-derived cultured cell line capable of stably expressing cytochromes P450, the metabolic pathway of xenobiotics and/or endogenous substrates can be analyzed (J. L. Napoli et al., Methods in Enzymology, vol. 206, pp. 491–501, Ed. by M. R. Waterman et al., Academic Press, 1991; H. K. Kroemeret al., Methods in Enzymology, vol. 272, pp. 99–108, Ed. by M. R. Waterman et al., Academic Press, 1996).

The examples of the test specimen given above apply also to the specimen to be tested here.

(c) Method for Analyzing a Chemical Structure of the Metabolite of Xenobiotics and/or Endogenous Substrates:

By analyzing a change in the structure of xenobiotics and/or endogenous substrates caused upon exposure of a test specimen. e.g., to the human hepatic carcinoma-derived cultured cell line capable of stably expressing cytochromes P450, the chemical structure of the metabolite of xenobiotics and/or endogenous substrates can be analyzed (J. L. Napoli et al., Methods in Enzymology, vol. 206, pp. 491–501, Ed. by M. R. Waterman et al., Academic Press, 1991; H. K. Kroemer et al., Methods in Enzymology, vol. 272, pp. 99–108, Ed. by M. R. Waterman et al., Academic Press, 1996).

The examples of the test specimen given above apply also to the specimen to be tested here.

(d) Method for Preparing the Metabolite of Xenobiotics and/or Endogenous Substrates:

By collecting the altered product (the so-called metabolite) from xenobiotics and/or endogenous substrates produced as a result of exposing a test specimen, e.g., to the human hepatic carcinoma-derived cultured cell line capable of stably expressing cytochromes P450 and purifying and isolating the product in an appropriate manner, the metabolite of xenobiotics and/or endogenous substrates can be prepared (J. L. Napoli et al., Methods in Enzymology, vol. 206, pp. 491–501, Ed. by M. R. Waterman et al., Academic Press, 1991).

The examples of the test specimen given above apply also to the specimen to be tested here.

(e) Method for Analyzing Inhibition of the Metabolizing Enzyme for Xenobiotics and/or Endogenous Substrates:

By exposing a test specimen, e.g., to the human hepatic carcinoma-derived cultured cell line capable of stably expressing cytochromes P450, the inhibition of a metabolizing enzyme for xenobiotics and/or endogenous substrates can be analyzed (J. L. Napoli et al., Methods in Enzymology, vol. 206, pp. 491–501, Ed. by M. R. Waterman et al., Academic Press, 1991). Specifically, the inhibition can be detected by the inhibition of cytochromes P450 enzyme activity, reduction in the amount of protein, decreased mRNA, etc. The detection may be made using publicly known methods, including an assay for enzyme activity corresponding to the respective members of P450, Western blotting corresponding to the respective P450 proteins, Northern hybridization corresponding to various P450 mRNAs, RT-PCR, etc.

The examples of the test specimen given above apply also to the specimen to be tested here.

(f) Method for Analyzing an Accelerated Activity of the Metabolizing Enzyme for Xenobiotics and/or Endogenous Substrates:

By exposing a test specimen, e.g., to the human hepatic carcinoma-derived cultured cell line capable of stably expressing cytochromes P450 and detecting the increased enzyme activity in the metabolism of xenobiotics and/or endogenous substrates, the increased amount of the enzyme or the increased amount of transcription in gene encoding the enzyme, the accelerated activity of the metabolizing enzyme for xenobiotics and/or endogenous substrates can be analyzed (J. Rueffet al., Mutation Research, 353 (1996) 151–176). Specifically, the accelerated activity can be analyzed by detecting the increased enzyme activity of cytochromes P450, the increased amount of protein or the increased mRNA. The detection may be made using publicly known methods, including Western blotting corresponding to the respective P450 proteins, Northern hybridization corresponding to various P450 mRNAs, RT-PCR, etc.

The examples of the test specimen given above apply also to the specimen to be tested here.

(g) Method for Analyzing Cytotoxicity by the Metabolism of Xenobiotics and/or Endogenous Substrates:

By exposing a test specimen, e.g., to the human hepatic carcinoma-derived cultured cell line capable of stably expressing cytochromes P450, the cytotoxicity caused by the metabolism of xenobiotics and/or endogenous substrates can be analyzed. Specifically, the cytotoxicity can be analyzed by observing a morphological change of the cell caused upon exposure of a test specimen; a change in viable cell count determined by publicly known methods including the MTT assay, Trypan Blue staining, Crystal Blue staining, etc.; leakage of intracellular enzyme such as lactose dehydrogenase; a change in structure of cells in the top layer; a change in intracellular enzyme, etc. (D. Wu, et al., Journal of Biological Chemistry, 271 (1996), 23914–23919).

The examples of the test specimen given above apply also to the specimen to be tested here.

(h) Method for Analyzing Expression of Genotoxicity by the Metabolism of Xenobiotics and/or Endogenous Substrates:

By exposing a test specimen, e.g., to the human hepatic carcinoma-derived cultured cell line capable of stably expressing cytochromes P450 and then subjecting the cells to the chromosomal aberration test or the micronucleus test, the genotoxicity caused by the metabolism of xenobiotics and/or endogenous substrates can be analyzed. The genotoxicity can also be analyzed by exposing a test specimen to the human hepatic carcinoma-derived cultured cell line capable of stably expressing cytochromes P450 and then subjecting the cells to the chromosomal aberration test, to the micronucleus test or to the reverse mutation test. This involves assessment of the test specimen altered by the cells in an appropriate assessment system (J. Rueffet al., Mutation Research, 353 (1996) 151–176; M. E. McManus et al., Methods in Enzymology, vol. 206, pp. 501–508, Ed by M. R. Waterman et al., Academic Press, 1991).

The examples of the test specimen given above apply also to the specimen to be tested here.

(i) Method for Analyzing Carcinogenicity by the Metabolism of a Xenobiotic and/or Endogenous Substrate:

By exposing a test specimen, e.g., to the human hepatic carcinoma-derived cultured cell line capable of stably expressing cytochromes P450 and then subjecting the cells to the chromosomal aberration test or to DNA modification, the carcinogenicity caused by the metabolism of xenobiotics and/or endogenous substrates can be analyzed. The carcinogenicity can also be analyzed by exposing a test specimen to the human hepatic carcinoma-derived cultured cell line capable of stably expressing cytochromes P450, followed by assessment of the test specimen altered by the cells in an appropriate system for evaluating carcinogenesis (J. Rueffet al., Mutation Research, 353 (1996) 151–176; K. Kawajiri, et al., Cytochromes, P450, Metabolic and Toxicological Aspects, pp. 77–98, ed. by C. Ioannides, CRC Press (1996)).

The examples of the test specimen given above apply also to the specimen to be tested here.

(j) Method for Analyzing Mutagenicity by the Metabolism of Xenobiotics and/or Endogenous Substrates:

By exposing a test specimen, e.g., to the human hepatic carcinoma-derived cultured cell line capable of stably expressing cytochromes P450 and then subjecting the cells to the chromosomal aberration test or the micronucleus test, the mutagenicity by the metabolism of xenobiotics and/or endogenous substrates can be analyzed. The mutagenicity can also be analyzed by exposing a test specimen to the human hepatic carcinoma-derived cultured cell line capable of stably expressing cytochromes P450 and then subjecting the cells to the chromosomal aberration test, the micronucleus test or the reverse mutation test, which involves assessment of the test specimen altered by the cells in an appropriate assessment system (J. Rueff et al., Mutation Research, 353 (1996) 151–176).

The examples of the test specimen given above apply also to the specimen to be tested here.

(k) Method for Analyzing Hepatotoxicity by the Metabolism of Xenobiotics and/or Endogenous Substrates:

The hepatotoxicity by the metabolism of xenobiotics and/or endogenous substrates can be analyzed by exposing a test specimen, e.g., to the human hepatic carcinoma-derived cultured cell line capable of stably expressing cytochromes P450 and then observing the expression of cytotoxicity. Alternatively, it can be analyzed by exposing a test specimen to the human hepatic carcinoma-derived cultured cell line capable of stably expressing cytochromes P450, administering the test specimen altered by the cells to other liver cells, liver slices or removed liver or to an experimental animal and then observing a change in cell or tissue or an in vivo change caused thereby.

The examples of the test specimen given above apply also to the specimen to be tested here.

(l) Method for Analyzing Xenobiotics and/or Endogenous Substrates that Act on the Liver:

The expression of the action on the liver can be analyzed either by exposing a test specimen, e.g., to the human hepatic carcinoma-derived cultured cell line capable of stably expressing cytochromes P450 and then observing the expression of a change in the cells caused, or by exposing a test specimen to the human hepatic carcinoma-derived cultured cell line capable of stably expressing cytochromes P450, administering the test specimen altered by the cells to other liver cells, liver slices or removed liver or to experimental animal and then observing a change in cell or tissue or an in vivo change caused thereby.

The examples of the test specimen given above apply also to the specimen to be tested here.

Furthermore, the present invention provides a method for screening a substance, which comprises using the human hepatic carcinoma-derived cultured cell line capable of stably expressing cytochromes P450, as well as a compound or its salt obtainable by the screening method, wherein the substance to be screened is (A) a substance capable of inhibiting the metabolizing enzyme for xenobiotics and/or endogenous substrates, (B) a substance capable of accelerating an activity of the metabolizing enzyme for xenobiotics and/or endogenous substrates, (C) a substance capable of expressing cytotoxicity by the metabolism of xenobiotics and/or endogenous substrates, (D) a substance capable of expressing genotoxicity by the metabolism of xenobiotics and/or endogenous substrates, (E) a substance capable of expressing carcinogenicity by the metabolism of xenobiotics and/or endogenous substrates, (F) a substance capable of expressing mutagenicity by the metabolism of xenobiotics and/or endogenous substrates, (G) a substance capable of expressing hepatotoxicity by the metabolism of xenobiotics and/or endogenous substrates, (H) xenobiotics and/or endogenous substrates which act on the liver, or (I) a substance capable of acquiring a new physiological activity or increasing or decreasing the inherent physiological activity, through the metabolism of xenobiotics and/or endogenous substrates.

(A) According to the method for screening a substance capable of inhibiting the metabolizing enzyme for xenobiotics and/or endogenous substrates, the inhibition is analyzed by the method described in (e) above for analyzing the inhibition of a metabolizing enzyme for xenobiotics and/or endogenous substrates, in which such a substance that inhibits the enzyme activity of cytochromes P450, reduces the amount of protein or reduces mRNA can be selected as the substance capable of inhibiting the enzyme activity for xenobiotics and/or endogenous substrates.

(B) According to the method for screening a substance capable of accelerating an activity of the metabolizing enzyme for xenobiotics and/or endogenous substrates, the acceleration is analyzed by the method described in (f) above for analyzing the acceleration of a metabolizing enzyme for xenobiotics and/or endogenous substrates, in which such a substance that accelerates the enzyme activity of cytochromes P450, increases the amount of protein or increases mRNA can be selected as the substance capable of inhibiting the enzyme activity for xenobiotics and/or endogenous substrates.

(C) According to the method for screening a substance capable of expressing cytotoxicity by the metabolism of xenobiotics and/or endogenous substrates, the cytotoxicity is analyzed by the method described in (g) above for analyzing the cytotoxicity by the metabolism of xenobiotics and/or endogenous substrates, in which such a substance that causes, e.g. a morphological change of the cell upon exposure of a test specimen, a change in viable cell count, leakage of intracellular enzyme, a change in structure of cells in the top layer, a change In intracellular enzyme. etc. can be selected as the substance capable of expressing the cytotoxicity by the metabolism of xenobiotics and/or endogenous substrates.

(D) According to the method for screening a substance capable of expressing genotoxicity by the metabolism of xenobiotics and/or endogenous substrates, the genotoxicity can be analyzed by the method described in (h) above for analyzing the genotoxicity by the metabolism of xenobiotics and/or endogenous substrates, in which such a test specimen that causes genotoxicity through the metabolism of xenobiotics and/or endogenous substrates by subjecting to, e.g., the chromosomal aberration test or the micronucleus test can be selected as a substance capable of expressing the genotoxicity by the metabolism of xenobiotics and/or endogenous substrates.

(E) According to the method for screening a substance capable of expressing carcinogenicity by the metabolism of xenobiotics and/or endogenous substrates, the carcinogenicity can be analyzed by the method described in (i) above for analyzing the carcinogenicity by the metabolism of xenobiotics and/or endogenous substrates, in which such a test specimen that causes carcinogenicity through the metabolism of xenobiotics and/or endogenous substrates by subjecting to, e.g., the chromosomal aberration test or the DNA modification can be selected as a substance capable of expressing the carcinogenicity by the metabolism of xenobiotics and/or endogenous substrates.

(F) According to the method for screening a substance capable of expressing mutagenicity by the metabolism of xenobiotics and/or endogenous substrates, the mutagenicity can be analyzed by the method described in (j) above for analyzing the mutagenicity by the metabolism of xenobiotics and/or endogenous substrates, in which such a is test specimen that causes mutagenicity through the metabolism of xenobiotics and/or endogenous substrates by subjecting to, e.g., the chromosomal aberration test or the micronucleus test can be selected as a substance capable of expressing the mutagenicity by the metabolism of xenobiotics and/or endogenous substrates.

(G) According to the method for screening a substance capable of expressing hepatotoxicity by the metabolism of xenobiotics and/or endogenous substrates, the hepatotoxicity can be analyzed following the method described in (k) above for analyzing the hepatotoxicity by the metabolism of xenobiotics and/or endogenous substrates, which involves, e.g., exposing a test specimen to cells, administering the test specimen altered by the cells to other liver cells, liver slices, removed liver or experimental animal, and observing a change in cells or tissues or a change in vivo. Such a test specimen that causes hepatotoxicity through the metabolism of xenobiotics and/or endogenous substrates can be selected as a substance capable of expressing the hepatotoxicity by the metabolism of xenobiotics and/or endogenous substrates.

(H) According to the method for screening xenobiotics and/or endogenous substrates which act on the liver, substances are analyzed by the method described in (l) above for analyzing xenobiotics and/or endogenous substrates which act on the liver, which involves, e.g., exposing a test specimen to a cell, administering the test specimen altered by the cell to other liver cells, liver slices, removed liver or experimental animal and then observing a change in cells or tissue or a change in vivo thereby. Thus, the xenobiotics and/or endogenous substrates which act on the liver can be screened.

(I) According to the method for screening a substance capable of acquiring a new physiological activity or increasing or decreasing the inherent physiological activity (including a so-called prodrug) through the metabolism of xenobiotics and/or endogenous substrates, the screening can be effected following the method described in (c) above for analyzing the chemical structure of the metabolite of xenobiotics and/or endogenous substrates and observing the physiological activity of the metabolite.

The compound or its salt that is obtainable by the screening methods described in (A) through (I) above is the compound or its salt selected from the test specimens that cause the activities, properties, etc. described above. Since these compounds are effective for the treatment and prevention of diseases (e.g., hepatic dysfunction) associated with metabolic aberration of xenobiotics in the liver, these compounds may be used as safe and low toxic pharmaceutical composition for the treatment and prevention of such diseases.

The compounds obtained by the screening methods above may be in the form of salts. As such salts of the compounds, there are salts with physiologically acceptable acids (e.g. inorganic acids or organic acids) or bases (e.g., alkaline metals), with physiologically acceptable acid additions salts being particularly preferred. Examples of such salts include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

Pharmaceutical compositions comprising the compounds or salts thereof obtained by the screening methods may be manufactured by publicly known methods or those similar thereto. Since the pharmaceutical compositions thus obtained are safe and low toxic, the compositions can be administered, e.g., to human or another mammal (e.g., rat, mouse, guineapig, rabbit, sheep, swine, bovine, horse, cat, dog, monkey, etc.).

The dose of the compound or its salts may vary depending on target disease, subject to be administered, routes for administration, etc.; for the purpose of treating, e.g., hepatic dysfunction by oral administration of the compound, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc.; when administered in the form of an injection for the purpose of treating, e.g., hepatic dysfunction, it is advantageous to administer the compound intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

Specific examples of pharmaceutical preparations available for the form given above include tablets (including sugar coated tablets and film coated tablets), pills, capsules (including microcapsules), granules, fine granules, powders, syrup, emulsion, suspension, injections, inhalation, ointments, etc. These pharmaceutical preparations are prepared in a conventional manner (e.g., following the methods described in the Japanese Pharmacopoeia).

In the pharmaceutical preparation above, the amount of the compound or its salt obtained by the screening methods above may vary depending on the form of preparation but in general, is within a range of 0.01 to 100 wt %, preferably 0.1 to 50 wt %, more preferably 0.5 to 20 wt %. based on the total weight of the pharmaceutical preparation.

Specifically, tablets may be manufactured by subjecting drugs directly to compression molding, or by adding to the drugs an excipient, a binder, a disintegrator or other suitable additives, uniformly blending the resulting mixture, grinding to granules, adding a lubricant to the granules and then subjecting to compression molding. Alternatively, drugs may be subjected directly to compression molding; or an excipient, a binder, a disintegrator or other suitable additives are added to the drugs, uniformly blended and finally compression-molded. The pharmaceutical preparation may also be prepared by subjecting granules previously made directly to compression molding or after adding suitable additives to the granules and uniformly blending them. The pharmaceutical preparation may also be added with, if desired, a coloring agent, a corrigent, etc. Furthermore, the pharmaceutical preparation may also be coated with an appropriate coating agent.

To prepare injection, a predetermined amount of the medicament is dissolved, suspended or emulsified in water for injection, physiological saline, Ringer's fluid, etc., or usually in vegetable oil when using a non-aqueous solvent. Thus, the medicament is adjusted to a prescribed amount. Alternatively, injection may also be prepared by taking the medicament in a predetermined amount and sealing it into a container for injection.

Examples of carriers that may be used for oral preparations include those conventionally used in pharmaceutical preparations such as starch, mannitol, crystalline cellulose, carboxymethyl cellulose, etc. Examples of carriers for injection are distilled water, physiological saline, a glucose solution, fluid supplementation, etc. Other additives conventionally used for pharmaceutical preparations in general may also be added appropriately to the preparations.

The present invention further provides the following features.

(1) A method for analysis which comprises using at least two cultured cell lines derived from human liver capable of stably expressing at least one of CYP1A1, CYP1A2, CYP2A6, CYP2B6, CYP2C8, CYP2C9, CYP2C19, CYP2D6, CYP2E1 and CYP3A4, said analysis being for (a) an enzyme that participates in the metabolism of xenobiotics and/or endogenous substrates, (b) a metabolic pathway of xenobiotics and/or endogenous substrates, (c) a chemical structure of the metabolite of xenobiotics and/or endogenous substrates, (d) inhibition of the metabolizing enzyme for xenobiotics and/or endogenous substrates, (e) an accelerated activity of the metabolizing enzyme for xenobiotics and/or endogenous substrates, (f) cytotoxicity by the metabolism of xenobiotics and/or endogenous substrates, (g) genotoxicity by the metabolism of xenobiotics and/or endogenous substrates, (h) carcinogenicity by the metabolism of a xenobiotic and/or endogenous substrate, (i) mutagenicity by the metabolism of xenobiotics and/or endogenous substrates, (j) hepatotoxicity by the metabolism of xenobiotics and/or endogenous substrates, or (k) xenobiotics and/or endogenous substrates that act on the liver.

(2) A method for preparation of the metabolite of xenobiotics and/or endogenous substrates, which comprises using at least two cultured cell lines from human liver capable of stably expressing at least one of CYP1A1, CYP1A2, CYP2A6, CYP2B6, CYP2C8, CYP2C9, CYP2C19, CYP2D6, CYP2E1 and CYP3A4.

(3) A method for screening a substance which comprises using at least two cultured cell lines from human liver capable of stably expressing at least one of CYP1A1, CYP1A2, CYP2A6, CYP2B6, CYP2C8, CYP2C9, CYP2C19, CYP2D6, CYP2E1 and CYP3A4, said substance being (a) a substance capable of inhibiting the metabolizing enzyme for xenobiotics and/or endogenous substrates, (b) a substance capable of accelerating an activity of the metabolizing enzyme for xenobiotics and/or endogenous substrates, (c) a substance capable of expressing cytotoxicity by the metabolism of xenobiotics and/or endogenous substrates, (d) a substance capable of expressing genotoxicity by the metabolism of xenobiotics and/or endogenous substrates, (e) a substance capable of expressing carcinogenicity by the metabolism of xenobiotics and/or endogenous substrates, (f) a substance capable of expressing mutagenicity by the metabolism of xenobiotics and/or endogenous substrates, (g) a substance capable of expressing hepatotoxicity by the metabolism of xenobiotics and/or endogenous substrates, (h) xenobiotics and/or endogenous substrates which act on the liver, or (i) a substance capable of acquiring a new physiological activity or increasing or decreasing the inherent physiological activity, through the metabolism of xenobiotics and/or endogenous substrates.

(4) A compound or a salt thereof (pharmaceutical composition), which is obtainable using the method according to (3).

The following terms are used to refer to the same meanings as given hereinabove: the term "a method for screening (a) an enzyme that participates in the metabolism of xenobiotics and/or endogenous substrates, (b) a metabolic pathway of xenobiotics and/or endogenous substrates, (c) a chemical structure of the metabolite of xenobiotics and/or endogenous substrates, (d) inhibition of the metabolizing enzyme for xenobiotics and/or endogenous substrates, (e) an accelerated activity of the metabolizing enzyme for xenobiotics and/or endogenous substrates, (f) cytotoxicity by the metabolism of xenobiotics and/or endogenous substrates, (g) genotoxicity by the metabolism of xenobiotics and/or endogenous substrates, (h) carcinogenicity by the metabolism of a xenobiotic and/or endogenous substrate, (i) mutagenicity by the metabolism of xenobiotics and/or endogenous substrates, (j) hepatotoxicity by the metabolism of xenobiotics and/or endogenous substrates, or (k) xenobiotics and/or endogenous substrates that act on the liver," the term "a method for preparation of the metabolite of xenobiotics and/or endogenous substrates," the term "a method for screening (a) a substance capable of inhibiting the metabolizing enzyme for xenobiotics and/or endogenous substrates, (b) a substance capable of accelerating an activity of the metabolizing enzyme for xenobiotics and/or endogenous substrates, (c) a substance capable of expressing cytotoxicity by the metabolism of xenobiotics and/or endogenous substrates, (d) a substance capable of expressing genotoxicity by the metabolism of xenobiotics and/or endogenous substrates, (e) a substance capable of expressing carcinogenicity by the metabolism of xenobiotics and/or endogenous substrates, (f) a substance capable of expressing mutagenicity by the metabolism of xenobiotics and/or endogenous substrates, (g) a substance capable of expressing hepatotoxicity by the metabolism of xenobiotics and/or endogenous substrates. (h) xenobiotics and/or endogenous substrates which act on the liver, or (i) a substance capable of acquiring a new physiological activity or increasing or decreasing the inherent physiological activity, through the metabolism of xenobiotics and/or endogenous substrates" as well as the terms "a compound or its salt (pharmaceutical composition), which is obtainable by the method for screening (a) a substance capable of inhibiting the metabolizing enzyme for xenobiotics and/or endogenous substrates, (b) a substance capable of accelerating an activity of the metabolizing enzyme for xenobiotics and/or endogenous substrates, (c) a substance capable of expressing cytotoxicity by the metabolism of xenobiotics and/or endogenous substrates, (d) a substance capable of expressing genotoxicity by the metabolism of xenobiotics and/or endogenous substrates, (e) a substance capable of expressing carcinogenicity by the metabolism of xenobiotics and/or endogenous substrates, (f) a substance capable of expressing mutagenicity by the metabolism of xenobiotics and/or endogenous substrates, (g) a substance capable of expressing hepatotoxicity by the metabolism of xenobiotics and/or endogenous substrates, (h) xenobiotics and/or endogenous substrates which acts on the liver, or (i) a substance capable of acquiring a new physiological activity or increasing or decreasing the inherent physiological activity, through the metabolism of xenobiotics and/or endogenous substrates."

The method for analysis, the method for preparation and the method for screening, described above, which comprises "using at least two cultured cell lines derived from human liver capable of stably expressing at least one of CYP1A1, CYP1A2, CYP2A6, CYP2B6, CYP2C8, CYP2C9, CYP2C19, CYP2D6, CYP2E1 and CYP3A4" enable to achieve the analysis, preparation and screening in a way closer to in vivo, than in the case of using the cell line which expresses only one enzyme of CYP1A1, CYP1A2, CYP2A6, CYP2B6, CYP2C8, CYP2C9, CYP2C19, CYP2D6, CYP2E1 and CYP3A4.

When two kinds or more of the cell lines are used, the respective cell lines may be used at the same time, or independently followed by comparison between the respective results in the analysis, preparation and screening.

The cell lines Hepc/3A4.5, Hepc/2E1.3–8, Hepc/2C9.1, Hepc/2C8.46, Hepc/1A2.9 and Hepc/1A1.4, which were obtained in EXAMPLES later described, have been deposited with Institute for Fermentation (IFO) at 2-17-85, Juso Honcho, Yodogawa-ku, Osaka, as deposit numbers IFO 50502, 50503, 50504, 50505, 50506 and 50507, respectively, since Feb. 10, 1999, and with the Ministry of International Trade and Industry, Agency of Industrial Science and Technology, National Institute of Bioscience and Human Technology (NIBH) at 1-1-3, Tsukuba Higashi, Tsukuba-shi, Ibaraki, as deposit numbers FERM BP-7120, FERM BP-7121, FERM BP-7122, FERM BP-7123, FERM BP-7124 and FERM BP-7125, respectively, since Apr. 12, 2000. Hepc/2B6.68 and Hepc/2D6.39 have been deposited with Institute for Fermentation (IFO) at 2-17-85, Juso Honcho, Yodogawa-ku, Osaka, as deposit numbers IFO 50508 and 50509, respectively, since Feb. 15, 1999. and with the Ministry of International Trade and Industry, Agency of Industrial Science and Technology, National Institute of Bioscience and Human Technology (NIBH) at 1-1-3, Tsukuba Higashi, Tsukuba-shi, Ibaraki, as deposit numbers FERM BP-7126 and FERM BP-7127, respectively, since Apr. 12, 2000. Hepc/2A6L.9 and Hepc/2C19.12 have been deposited with Institute for Fermentation (IFO) at 2-17-85, Juso Honcho, Yodogawa-ku. Osaka, as deposit numbers IFO 50511 and 50512, respectively, since Feb. 15, 1999, and with the Ministry of International Trade and Industry, Agency of Industrial Science and Technology, National Institute of Bioscience and Human Technology (NIBH) at 1-1-3, Tsukuba Higashi, Tsukuba-shi, Ibaraki, as deposit numbers FERM BP-7128 and FERM BP-7129, respectively, since Apr. 12, 2000.

EXAMPLES

Hereinafter EXAMPLES of the present invention are described in detail but the invention is not deemed to be limited thereto. For genetic engineering, conventional procedures were conducted following the manual described in Sambrook et al. (Molecular Cloning: A Laboratory Manual, Cold Spring Harbor Laboratory Press), etc., unless otherwise indicated.

Example 1
Cloning of DNA Fragments Encoding Cytochromes P450 and Preparation of Expression Vector DNA fragments encoding human cytochromes P450 were cloned from complementary DNA (cDNA) library derived from human adult liver, using the established polymerase chain reaction (hereinafter PCR) method. The cDNA sequences of human cytochromes P450 to be cloned are available from the database of GeneBank. The accession numbers in GeneBank are K03191 for CYP1A1; M55053 or M38504 for CYP1A2; M33318 or M33316 for CYP2A6: M29874 or J02864 for CYP2B6; M17397 or J03472 for CYP2C8; M61857 or J05326 for CYP2C9; M61854 or J05326 for CYP2C19; X08006 or Y00300 for CYP2D6; J02625 for CYP2E1 and J04449 for CYP3A4.

Each of the cloned cDNAs was inserted into PcDNA3.1 (+) vector (Invtrogen Co.) CMV (cytomegalovirus) downstream its enhancer promoter along with the direction in which the promoter could function, to obtain 1A1/pcDNA3.1(+) inserted with CYP1A1, 1A2/pcDNA3. 1(+) inserted with CYP1A2, 2A6/pcDNA3.1(+) inserted with CYP2A6.2B6/pcDNA3.1(+) inserted with CYP2B6, 2C8/pcDNA3.1(+) inserted with CYP2C8, 2C9/pcDNA3.1(+) inserted with CYP2C9, 2C19/pcDNA3.1(+) inserted with CYP2C19, 2D6/pcDNA3.1(+) inserted with CYP2D6, 2E1/pcDNA3.1(+) inserted with CYP2E1 and 3A4/pcDNA3.1 (+) inserted with CYP3A4, respectively.

Example 2
Screening of Cells Capable of Expressing the High Activity of Cytochromes P450

HepG2 was maintained in DMEM (Dulbecco's Modified Eagle's medium) supplemented with 10% FCS (fetal calf serum; Bio Whittaker). HepG2 was inoculated on a 60 mm dish and grown 50–60% confluently in a $CO_2$ incubator followed by transfection of 2 μg of 1A1/pcDNA3.1(+), 1A2/pcDNA3.1(+), 2A6/pcDNA3.1(+), 2B6/pcDNA3.1(+), 2C8/pcDNA3.1(+), 2C9/pcDNA3.1(+), 2C19/pcDNA3.1 (+), 2D6/pcDNA3.1(+), 2E1/pcDNA3.1(+) or 3A4/pcDNA3.1(+) using lipofectamine reagent (GIBCO BRL). After incubating in 10% FCS-supplemented DMEM medium for 2 days, the medium was replaced with fresh DMEM medium supplemented with 500 μg/ml G418 (GIBCO BRL) and 10% FCS. The medium was replaced every 3 or 4 days to effect cloning of G418-resistant strains. The resulting G418-resistant strains were maintained in DMEM medium supplemented with 200 μg/ml G418 (GIBCO BRL) and 10% FCS. Each of the G418-resistant strains was assayed for the activity of cytochromes P450 by the method described below. Cell lines showing a high activity were measured and cells that expressed the high activity were selected.

(1) Assay for Activity of CYP1A1- and CYP1A2-expressing Cells and Selection of Cells Expressing High Activity:

Ethoxyresorufin (Molecular Probes) was diluted with DMSO (dimethyl sulfoxide; Wako Junyaku K. K.) in a concentration of 2 mM. Then the dilution was further diluted to 500 μM with Phenol Red-free DMEM medium (GIBCO BRL) supplemented with 2% FCS (Bio Whittaker).

CYP1A1- or CYP1A2-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, Ethoxyresorufin previously diluted to 500 μM was added in 500 μl/well. After reacting at 37° C. in the dark, the reaction solution was recovered from each well. After 1800 μl of methanol (Wako Junyaku K. K) was added to 300 μl of the reaction solution and insoluble material was removed by centrifugation, fluorescent intensity was measured at an excited wavelength of 550 nm and a fluorescence wavelength of 586 nm using a spectrofluorometer to quantify the resorufin formed. The product purchased from Molecular Probes was used as the standard substance for resorufin (Molecular Probes).

From the CYP1A1 or CYPA2 activity-expressing strains, strains Hepc/1A1.4 and Hepc/1A2.9 were selected, respectively, as CYP1A1- and CYP1A2-expressing strains in high levels.

(2) Assay for Activity of CYP2A6-expressing Cells and Selection of Cells Expressing High Activity:

Coumarin (Wako Junyaku K. K.) was diluted with methanol (Wako Junyaku K. K.) in a concentration of 50 mM. Next, the dilution was further diluted to 500 μM with Phenol Red-free DMEM medium (GIBCO BRL) supplemented with 2% FCS (Bio Whittaker).

CYP2A6-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, coumarin previously diluted to 500 μM was added in 500 μl/well. After reacting at 37° C., the reaction solution was recovered from each well. The reaction solution was diluted to 10-fold with 0.1M Tris-HCl (pH 7.4) and fluorescent intensity was measured at an excited wavelength of 390 nm and a fluorescence wavelength of 440 nm using a spectrofluorometer to quantify 7-hydroxycoumarin formed. The product purchased from Extrasynthese was used as the standard substance for 7-hydroxycoumarin.

From the CYP2A6 activity-expressing strains, Hepc/2A6L.9 was selected as CYP2A6-expressing strain in a high level.

(3) Assay for Activity of CYP2B6-expressing Cells and Selection of Cells Expressing High Activity:

7-Ethoxycoumarin (Molecular Probes) was diluted with DMSO (Wako Junyaku K. K.) in a concentration of 10 mM. Next, the dilution was further diluted to 500 μM with Phenol Red-free DMEM medium (GIBCO BRL) supplemented with 2% FCS (Bio Whittaker).

CYP2B6-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, 7-ethoxycoumarin previously diluted to 500 μM was added in 500 μl/well. After reacting at 37° C., the reaction solution was recovered from each well. The reaction solution was diluted to 10-fold with 0.1M Tris-HCl (pH 7.4) and fluorescent intensity was measured at an excited wavelength of 390 nm and a fluorescence wavelength of 440 nm, using a spectrofluorometer (Hitatchi Spectrofluorometer F-2000) to quantify 7-hydroxycoumarin formed. The product purchased from Extrasynthese was used as the standard substance for 7-hydroxycoumarin.

From the CYP2B6 activity-expressing strains, Hepc/2B6.68 was selected as CYP2B6-expressing strain in a high level.

(4) Assay for Activity of CYP2C8-expressing Cells and Selection of Cells Expressing High Activity:

Taxol (ULTRAFINE Chemicals) was diluted with methanol (Wako Junyaku K. K. ) in a concentration of 10 mM. Next, the dilution was further diluted to 30 μM with Phenol Red-free DMEM medium (GIBCO BRL) supplemented with 2% FCS (Bio Whittaker).

CYP2C8-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, taxol diluted previously to 30 μM was added in 500 μl/well. After reacting at 37° C., the reaction solution was recovered from each well. After an equal volume of acetonitrile (Wako Junyaku K. K.) was added to and mixed with the reaction solution, insoluble material was removed by centrifugation. 6α-Hydroxypaclitaxel formed in the reaction solution was quantified on HPLC.

Capcell Pak C18 AG120 (5 μm, 4.6 mmφ×250 mm, Shiseido) was used as a column. As a mobile phase, 40% acetonitrile (reagent for HPLC, Wako Junyaku K. K. ) was used. After injecting 40 μl of the reaction solution, elution was conducted at a flow rate of 1.0 ml/min. and a column temperature of 40° C., using the mobile phase described above. Taxol and 6α-hydroxypaclitaxel were detected at 230 nm (absorbance). As the standard substance, 40 μl each of 10 μM taxol and 5 μM 6α-hydroxypaclitaxel (Gentest) were injected.

From the CYP2C8 activity-expressing strains, Hepc/2C8.46 was selected as CYP2C8-expressing strain in a high level.

(5) Assay for Activity of CYP2C9-expressing Cells and Selection of Cells Expressing High Activity:

Tolbutamide (Research Biochemicals International) was diluted with methanol (Wako Junyaku K. K. ) in a concentration of 50 mM. Next, the dilution was further diluted to 500 μM with Phenol Red-free DMEM medium (GIBCO BRL) supplemented with 2% FCS (Bio Whittaker).

CYP2C9-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, tolbutamide previously diluted to 500 μM was added in 500 μl/well. After reacting at 37° C., the reaction solution was recovered from each well. After an equal volume of acetonitrile (Wako Junyaku K. K.) was added to and mixed with the reaction solution, insoluble material was removed by centrifugation. Hydroxytolbutamide formed in the reaction solution was quantified on HPLC.

Inertsil ODS-2 (5 μm, 4.6 mmφ×150 mm, GL Science) was used as a column. As a mobile phase, a 72:28 v/v mixture of 10 mM acetate buffer (pH 4.3) and acetonitrile (reagent for HPLC, Wako Junyaku K. K.) was used. After injecting 40 µl of the reaction solution, elution was conducted at a flow rate of 1.0 ml/min. and a column temperature of 40° C., using the mobile phase described above. Tolbutamide and hydroxytolbutamide were detected at 230 nm (absorbance). As the standard substance, 40 µl each of 100 µM tolbutamide and 10 µM hydroxytolbutamide (Sumitomo Chemical Analysis Center) were injected.

From the CYP2C9 activity-expressing strains, Hepc/2C9.1 was selected as CYP2C9-expressing strain in a high level.

(6) Assay for Activity of CYP2C19-expressing Cells and Selection of Cells Expressing High Activity:

(S)-Mephenytoin (Sumitomo Chemical Analysis Center) was diluted with methanol (Wako Junyaku K. K.) in a concentration of 10 mM. Next, the dilution was further diluted to 100 µM with Phenol Red-free DMEM medium (GIBCO BRL) supplemented with 2% FCS (Bio Whittaker).

CYP2C19-expressing cells were inoculated on a 12-well plate (Falcon an incubated in a $CO_2$ incubator so as to become confluent. After incubation, the medium was suctioned and cells adhering to the plate were washed with Phenol Red-free DMEM medium. Subsequently, mephenytoin previously diluted to 100 µM was added in 500 µl/well. After reacting at 37° C., the reaction solution was recovered from each well. After an equal volume of acetonitrile (Wako Junyaku K. K.) was added to and mixed with the reaction solution, insoluble material was removed by centrifugation. 4'-Hydroxymephenytoin formed in the reaction solution was quantified on HPLC.

Capcell Pak C18 AG120 (5 µm, 4.6 mmφ×250 mm, Shiseido) was used as a column. As a mobile phase, a 74:26 v/v mixture of 0.05 M $KH_2PO_4$ (pH 4.0) and acetonitrile (reagent for HPLC, Wako Junyaku K. K.) was used. After injecting 40 µl of the reaction solution, elution was conducted at a flow rate of 0.8 ml/min. and a column temperature of 40° C., using the mobile phase described above. (S)-Mephenytoin and 4'-hydroxymephenytoin were detected at 204 nm (absorbance). As the standard substance, 40 µl each of 50 µM (S)-mephenytoin and 5 µM hydroxymephenytoin (Sumitomo Chemical Analysis Center) were injected.

From the CYP2C19 activity-expressing strains, Hepc/2C19.12 was selected as CYP2C19-expressing strain in a high level.

(7) Assay for Activity of CYP2D6-expressing Cells and Selection of Cells Expressing High Activity:

Bufralol (Sumitomo Chemical Analysis Center) was diluted with distilled water in a concentration of 20 mM. Next, the dilution was further diluted to 200 µM with Phenol Red-free DMEM medium (GIBCO BRL) supplemented with 2% FCS (Bio Whittaker).

CYP2D6-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, bufralol previously diluted to 200 µM was added in 500 µl/well. After reacting at 37° C., the reaction solution was recovered from each well and 1'-hydroxybufralol formed in the reaction solution was quantified on HPLC.

Inertsil ODS (5 µm, 4.6 mmφ×250 mm, GL Science) was used as a column. As a mobile phase, 30% acetonitrile (reagent for HPLC, Wako Junyaku K. K.) containing 1 mM perchloric acid (Wako Junyaku K. K.) was used. The reaction solution was diluted to 100-fold with distilled water and 40 µl of the reaction solution was injected, followed by elution at a flow rate of 1.0 ml/min. and a column temperature of 50° C., using the mobile phase described above. Bufralol and hydroxybufralol were detected at an excited wavelength of 252 nm and at a fluorescence wavelength of 302 nm. As the standard substance, 40 µl each of 100 pM bufralol and 10 pM 1'-hydroxybufralol (Sumitomo Chemical Analysis Center) were injected.

From the CYP2D6 activity-expressing strains, Hepc/2D6.39 was selected as CYP2D6-expressing strain in a high level.

(8) Assay for Activity of CYP2E1-expressing Cells and Selection of Cells Expressing High Activity:

p-Nitrophenol (Wako Junyaku K. K.)) was diluted with DMSO (Wako Junyaku K. K.) in a concentration of 2 mM. Next, the dilution was further diluted to 500 µM with Phenol Red-free DMEM medium (GIBCO BRL) supplemented with 2% FCS (Bio Whittaker).

2E1-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, p-nitrophenol previously diluted to 500 µM was added in 500 µl/well. After reacting at 37° C., the reaction solution was recovered from each well. To 100 µl of the reaction solution 50 µl of NaOH (Wako Junyaku K. K.) was added, and insoluble material was removed by centrifugation. By measuring absorbance at 540 nm–620 nm, 4-nitrocatechol formed was quantified. 4-Nitrocatechol purchased from Wako Junyaku K. K. was used as the standard substance.

From the CYP2E1 activity-expressing strains, Hepc/2E1.3–8 was selected as CYP2E1-expressing strain in a high level.

(9) Assay for Activity of CYP3A4-expressing Cells and Selection of Cells Expressing High Activity:

Testosterone (Wako Junyaku K. K.) was diluted with methanol (Wako Junyaku K. K.) in a concentration of 10 mM. Next, the dilution was further diluted to 100 µM with Phenol Red-free DMEM medium (GIBCO BRL) supplemented with 2% FCS (Bio Whittaker).

CYP3A4-expressing cells were inoculated on a 12-well plate (Falcon) and incubated in a $CO_2$ incubator so as to become confluent. After incubation, the medium was suctioned and cells adhering to the plate were washed with Phenol Red-free DMEM medium. Subsequently, testosterone previously diluted to 100 µM was added in 500 µl/well. After reacting at 37° C., the reaction solution was recovered from each well. After an equal volume of acetonitrile (Wako Junyaku K. K.) was added to and mixed with the reaction solution, insoluble material was removed by centrifugation. 6β-Hydroxytestosterone formed in the reaction solution was quantified on HPLC.

Capcell Pak C18 AG120 (5 µm, 4.6 mmφ×250 mm, Shiseido) was used as a column. A solution of 40% methanol (reagent for HPLC, Wako Junyaku K. K.) and 3.5% acetonitrile (reagent for HPLC, Wako Junyaku K. K.), and a solution of 40% methanol and 20 acetonitrile were used as solution A and solution B, respectively. A program was made up to set for a linear gradient of 0–100% solution B in 0–20 minutes, 100% solution B in 20–30 minutes and since then 100% solution. By injecting 40 µl of the reaction solution, elution was performed at a flow rate of 1.0 ml/min. and a column temperature of 40° C., using the mobile phase described above. Testosterone and 6β-hydroxytestosterone were detected at 254 nm (absorbance). As the standard substance, 40 µl each of 50 µM testosterone and 5 µM 6β-hydroxytestosterone (Sumitomo Chemical Analysis Center) were injected.

From the CYP3A4 activity-expressing strains, Hepc/3A4.5 was selected as CYP3A4-expressing strain in a high level.

Example 3

Kinetic Analysis of Cytochromes P450-expressing Strains in a High Level

Following the assay for enzyme activity described in EXAMPLE 2, a variety of substrates were acted on the cytochromes P450-expressing strains in a high level, which were obtained in EXAMPLE 2. A Lineweaver-Burk plot was prepared, and Km and Vmax values were obtained from the X- and Y-intercepts. The results are shown in TABLE 1.

TABLE 1

| CYP molecules | Transformant | Enzyme activity | Rate Constant | |
|---|---|---|---|---|
| | | | Km ($\mu$M) | Vmax (pmol/min/mg) |
| CYP1A1 | Hepc/1A1.4 | 7-ethoxyresorufin O-deethylase activity | 0.25 | 56 |
| CYP1A2 | Hepc/1A2.9 | 7-ethoxyresorufin O-deethylase activity | 0.72 | 1.6 |
| CYP2A6 | Hepc/2A6L.9 | Coumarin 7-hydroxylase activity | 11.1 | 412 |
| CYP2B6 | Hepc/2B6.68 | 7-ethoxycoumarin O-deethylase activity | 81 | 80 |
| CYP2C8 | Hepc/2C8.46 | Taxol 6-hydroxylase activity | 7.4 | 0.009 |
| CYP2C9 | Hepc/2C9.1 | Tolbutamide 4-hydroxylase activity | 77 | 23 |
| CYP2C19 | Hepc/2C19.12 | (S)-mephenytoin 4'-hydroxylase activity | 8.26 | 140 |
| CYP2D6 | Hepc/2D6.39 | Bufuralol 1'-hydroxylase activity | 17 | 14 |
| CYP2E1 | Hepc/2E1.3–8 | p-nitrophenol hydroxylase activity | 88 | 120 |
| CYP3A4 | Hepc/3A4.5 | Testosterone 6β-hydroxylase activity | 96 | 71 |

Example 4

Activation of the Metabolism of Acetaminophen by CYP2E1-expressing Cells and Expression of Cytotoxicity Method:

1. MTT Assay

HepG2 or CYP2E1-expressing cells (Hepc/2E1.3–8) (4×10$^5$ cells/ml) were incubated with acetaminophen (Wako Junyaku K. K. ) diluted to a given concentration in DMEM medium supplemented with 5% FCS in a $CO_2$ incubator. In the test to terminate glutathione conjugation, L-Buthionine [S,R]-Sulfoximine (BSO, Sigma) was added to the medium in a final concentration of 100 $\mu$M. After incubation for 4 days, 20 $\mu$l of a solution of 3-(4,5-dimethyl-2-thiazolyl)-2,5-diphenyl-2H-tetrazolium bromide (MTT, Sigma) adjusted to 1 mg/ml with PBS (Flow) was added to each well followed by incubation at 37° C. for 3 hours. Next, 100 $\mu$l of 0.01N HCl solution containing 10% SDS was added to each well. After incubation at 37° C. overnight, absorbance was measured at 590 nm. The results are shown in FIG. 1.

2. Determination of LDH (Lactate Dehydrogenase) Leakage

Figure 2:
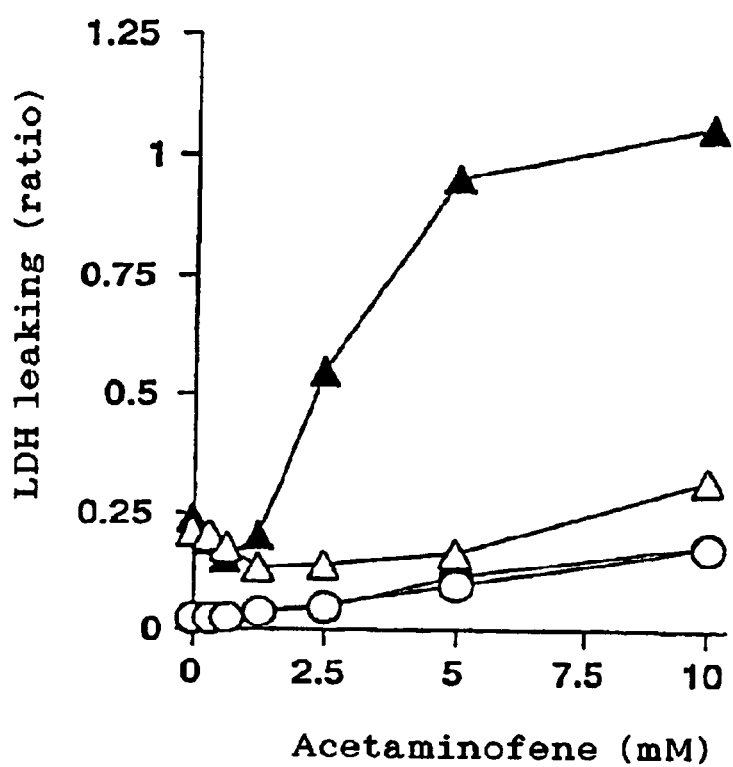
FIG. 2 shows the results by the LDH leakage test on expression of cytotoxicity of acetaminophen shown in EXAMPLE 4, wherein symbols -○-, -△-, -●- and -▲- denote HepG2, Hepc/2E1.3–8, HepG2+100 μM BSO and Hepc/2E1.3–8+100 μBSO, respectively.

Two plates each with the same design as in the MTT assay were prepared (for determination of LDH activity in the culture supernatant and for determination of LDH activity in the culture supernatant+LDH activity in the cells). After incubating for 3 days in a $CO_2$ incubator, 10 $\mu$l of the supernatant was taken from each well of one plate (for determination of LDH activity in the supernatant), transferred to another 96-well plate, and 40 $\mu$l of distilled water was further added. On the other hand, 10 $\mu$l of 10% Triton X100 (Wako Junyaku K. K. ) was added to each well of another plate (for determination of LDH activity in the culture supernatant+LDH activity in the cells), followed by shaking and incubation at 37° C. for 45 minutes. After centrifuging at 1500 rpm for 5 minutes, 10 $\mu$l of the supernatant was taken from each well, transferred to another 96-well plate, and 40 $\mu$l of distilled water was further added. The LDH activity of each well in these plates was measured using Cytotox 96 Non-Radioactive Cytotoxicity Assay Kit (Promega). Multiscanning MS-UV was used for the measurement of absorbance. A ratio of the LDH activity in the supernatant to (the LDH activity in the supernatant+ the LDH activity in the cells) was made an LDH leakage rate. The results are shown in FIG. 2.

Results: FIGS. 1 and 2

When acetaminophen is present in a large quantity, exhaustion of activated sulfate or a rate-determining factor occurs. While glucuronide conjugation occurs in large quantities, the reaction rate is limiting and thus, N-hydroxylation is caused by P450. The activated intermediate N-acetylbenzoquinonimide formed from the N-hydroxylated product is generally detoxified through conjugation with glutathione. It is known, however, that exhaustion of glutathione results in covalent binding of the activated intermediate with macromolecular components in the liver to cause necrosis of liver cells (M. J. J. Ronis et al., Cytochromes P450 Metabolic and Toxicological Aspects, pages 211–240, ed. by C. Ioannides et al., CRC Press, 1996).

Acetaminophen caused a slight leakage of LDH from HepG2 and Hepc/2E1.3–8 cells. When glutathione present in the cells was exhausted there in the presence of BSO, sensitivity to acetaminophen was enhanced approximately 4 times in Hepc/2E1.3–8 cells, and LDH was concentration-dependently leaked at a lower level. Any effect expected in the presence of BSO was not noted with HepG2 (FIG. 2). Turning to the MTT assay method, acetaminophen caused a slight decrease of the MTT activity in HepG2 and Hepc/2E1.3–8 cells. In the presence of BSO, an increased sensitivity to acetaminophen was noted in Hepc/2E1.3–8 cells, with concentration-dependently lowering of the MTT activity at a lower concentration (FIG. 1). While acetaminophen is metabolized by the CYP2E1 activity expressed by Hepc/2E1.3–8, the metabolites are detoxified through glutathione conjugation. However, when glutathione is exhausted through the action of BSO, it is considered that cytotoxicity would be exhibited by the metabolic intermediate formed. It is demonstrated that Hepc/2E1.3–8 has not only the CYP2E1 activity but also the glutathione transferase activity.

Example 5

Activation of the Metabolism of Benzanthracene by CYP1A1-expressing Cells and Expression of Cytotoxicity Method:

CYP1A1-expressing cells (Hepc/1A1.4) (4×10$^5$ cells/ml) were incubated with benzanthracene (Sigma) diluted to a given concentration in DMEM medium supplemented with 5% FCS in a $CO_2$ incubator. After incubation for 4 days, 20 $\mu$l of a MTT (Sigma) solution adjusted to 1 mg/ml with PBS (Flow) was added to each well followed by incubation at 37° C. for 3 hours. Next, 100 $\mu$l of 0.01N HCl solution containing 10% SDS was added to each well. After incubation at 37° C. overnight, absorbance was measured at 590 nm. The results are shown in FIG. 3.

Figure 3:
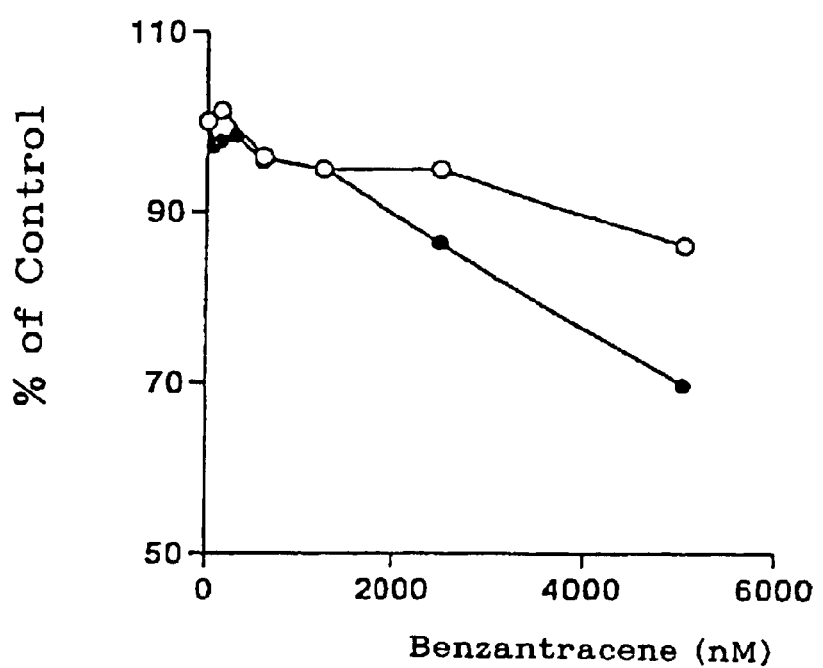
FIG. 3 shows the results by the MTT assay method relating to expression of cytotoxicity of benzanthracene shown in EXAMPLE 5, wherein symbols -○- and -●- denote HepG2 and Hepc/1A1.4, respectively.

Results: see FIG. 3

It is known that benzanthracene is metabolized by the CYP1A1 activity and the metabolic intermediate formed causes cytotoxicity, carcinogenesis and mutagenesis (K. Kawajiri, et al., Cytochromes P450 Metabolic and Toxicological Aspects, pages 77–97, ed. by C. Ioannides, et al., CRC Press, 1996). A more potent reduction in the MTT activity was noted in Hepc/1A1.4 cells than in HepG2, dependently with the concentration of benzanthracene. This reveals that benzanthracene was metabolized by the CYP1A1 activity expressed by Hepc/1A1.4 cells, and cytotoxicity was exhibited by the metabolic intermediate.

Example 6

Activation of the Metabolism of Cyclophosphamide by CYP2B6-expressing Cells and Expression of Citotoxicity Method:

1. MTT Assay

CYP2B6-expressing cells (Hepc/2B6.68)($4\times10^5$ cells/ml) were incubated with cyclophosphamide (Sigma) diluted to a given concentration in DMEM medium supplemented with 5% FCS in a $CO_2$ incubator. After incubation for 4 days, 20 μl of a MTT (Sigma) solution adjusted to 1 mg/ml with PBS (Flow) was added to each well followed by incubation at 37° C. for 3 hours. Next, 100 μl of 0.01N HCl solution containing 10% SDS was added to each well. After incubation at 37° C. overnight, absorbance was measured at 590 nm. The results are shown in FIG. 4.

2. Determination of LDH Leakage

Two plates each with the same design as in the MTT assay were prepared (for determination of LDH activity in the culture supernatant and for determination of LDH activity in the culture supernatant+LDH activity in the cells). After incubating for 4 days in a $CO_2$ incubator, 10 μl of the supernatant was taken from each well of one plate (for determination of LDH activity in the supernatant), transferred to another 96-well plate, and 40 μl of distilled water was further added. On the other hand, 10 μl of 10% Triton X100 was added to each well of another plate (for determination of LDH activity in the culture supernatant+LDH activity in the cells), followed by shaking and incubation at 37° C. for 45 minutes. After centrifuging at 1500 rpm for 5 minutes, 10 μl of the supernatant was taken from each well, transferred to another 96-well plate, and 40 μl of distilled water was further added. The LDH activity of each well in these plates was measured using Cytotox 96 Non-Radioactive Cytotoxicity Assay Kit (Promega). Multiscanning MS-UV was used for the measurement of absorbance. A ratio of the LDH activity in the supernatant to (the LDH activity in the supernatant + the LDH activity in the cells) was made an LDH leakage rate. The results are shown in FIG. 5.

Figure 4:
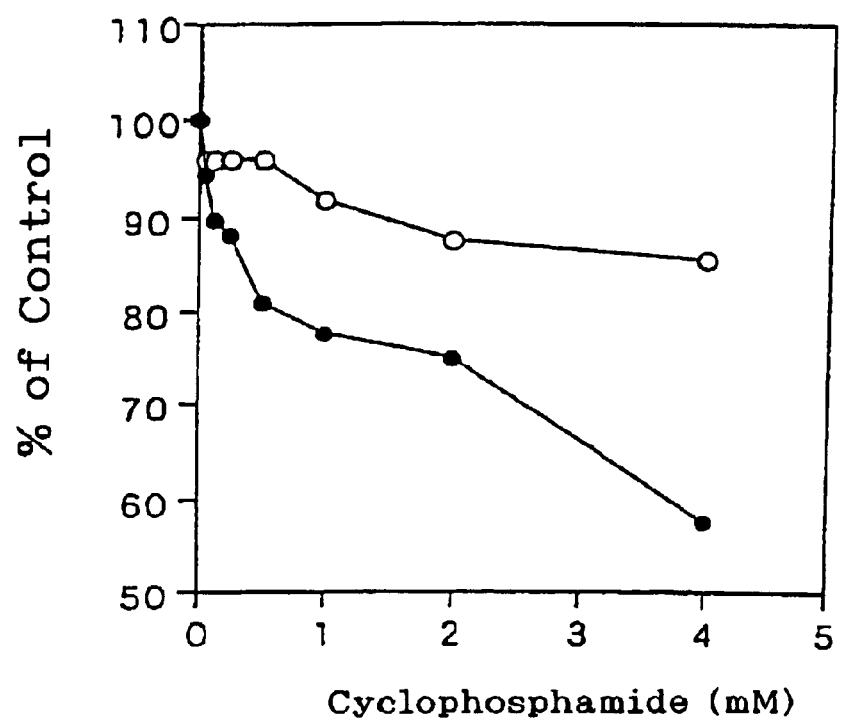
FIG. 4 shows the results by the MTT assay method relating to expression of cytotoxicity of cyclophosphamide shown in EXAMPLE 6, wherein symbols -○- and -●- denote HepG2 and Hepc/2B6.68, respectively.
Figure 5:
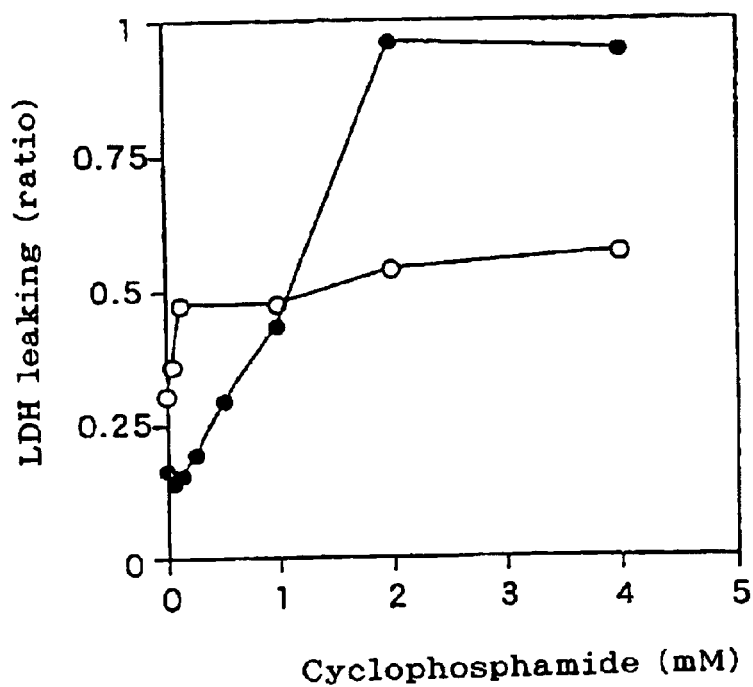
FIG. 5 shows the results by the LDH leakage test on expression of cytotoxicity of cyclophosphamide shown in EXAMPLE 6, wherein symbols -○- and -●- denote HepG2 and Hepc/2B6.68, respectively.

Results: see FIGS. 4 and 5

It is considered that after cyclophosphamide is hydrolyzed at the 4-position, phosphoramide or acrolein formed by non-enzymatic degradation would act as an alkylating agent to cause hepatic cytotoxicity triggered by covalent binding to macromolecular components in liver cells (K. H. Thomas, et al., Cancer Research, vol. 53, pages 5629–5637, 1993). Cyclophosphamide caused a leakage of LDH in Hepc/2B6.68 cells concentration-dependently in the concentration up to 2 mM and then reached the plateau at the following concentrations. Cyclophosphamide was slightly cytotoxic also in HepG2 (FIG. 4). Turning to the MTT assay method, cyclophosphamide caused a slight decrease of the MTT activity concentration-dependently in Hepc/2B6.68 cells (FIG. 5). Cyclophosphamide was metabolized by the CYP2B6 activity, and the metabolic intermediate formed showed cytotoxicity.

Example 7

Analysis of Inhibition of CYP3A4 Activity

Method:

Hepc/3A4.5 cells were inoculated on a 12-well plate and incubated so as to become confluent. After washing twice with Phenol Red-free DMEM medium, various concentrations of ketoconazole (Biomol Research Lab.) diluted with 500 μl of Phenol Red-free DMEM medium containing 2% FCS was added followed by incubation at 37° C. for 4 hours. After washing twice with Phenol Red-free DMEM medium, testosterone in a final cocentration of 100 μM diluted with 500 μl of Phenol Red-free DMEM medium containing 2% FCS was added. After incubation at 37° C. for an hour, the supernatant was recovered. After an equal volume of acetonitrile was added to and mixed with the reaction solution, insoluble matters were removed by centrifugation to provide for a test specimen. The thus obtained specimen was quantified for 6β-hydroxy-testosterone on HPLC by the method described in EXAMPLE 2 (9).

Figure 6:
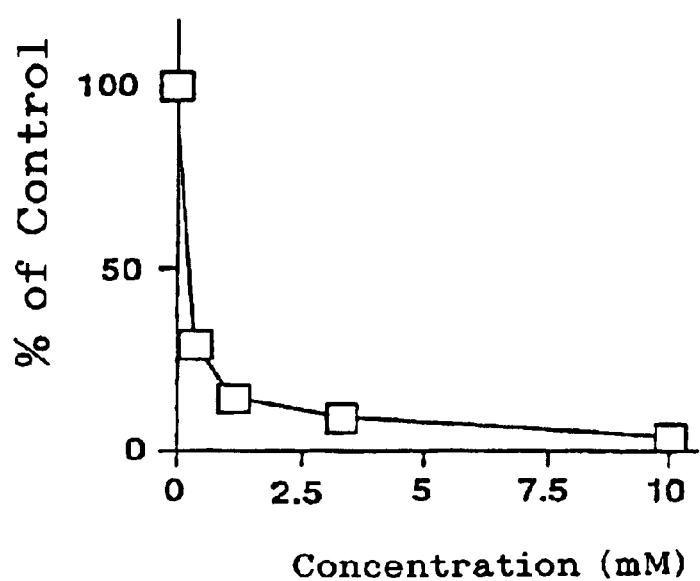
FIG. 6 shows the results of the test on inhibition of ketoconazole against the CYP3A4 activity shown in EXAMPLE 7, wherein symbol -□- denotes ketoconazole.

The experimental results are shown in terms of relative value when the amount of 6β-hydroxy-testosterone without adding any drug was made 100% (FIG. 6).

Ketoconazole is known to be a strong CYP3A4 inhibitor (S. J. Baldwin, et al., Xenobiotica, vol. 25, pages 261–270, 1995). The CYP3A4 activity (testosterone 6β-hydroxylation activity) was inhibited in Hepc/3A4.5 cells dependently on the concentration of ketoconazole (FIG. 6). $IC_{50}$ of ketoconazole was 0.3 μM or less.

Example 8

Analysis of CYP2E1 Activity Induction

Method:

Hepc/2E1.3–8 cells ($5\times10^5$ cells/ml) were inoculated with ethanol and DMSO (dimethylsulfoxide)(Wako Junyaku K. K. ) diluted with DMEM medium to a given concentration on a 12-well plate (Falcon) and incubated in a $CO_2$ incubator for 3 days. The medium was suctioned and the cells attached to the plate were washed with Phenol Red-free DMEM medium. Subsequently, p-nitrophenol previously diluted to 500 μM was added in 500 μl/well. After reacting at 37° C., the reaction solution was recovered from each well. To 100 μl of the reaction solution 50 μl of NaOH (Wako Junyaku K. K. ) was added, and insoluble matters were removed by centrifugation. By measuring absorbance at 540 nm–620 nm with multi-scanning MS-UV (Labo Systems), 4-nitrocatechol formed was quantified.

Figure 7:
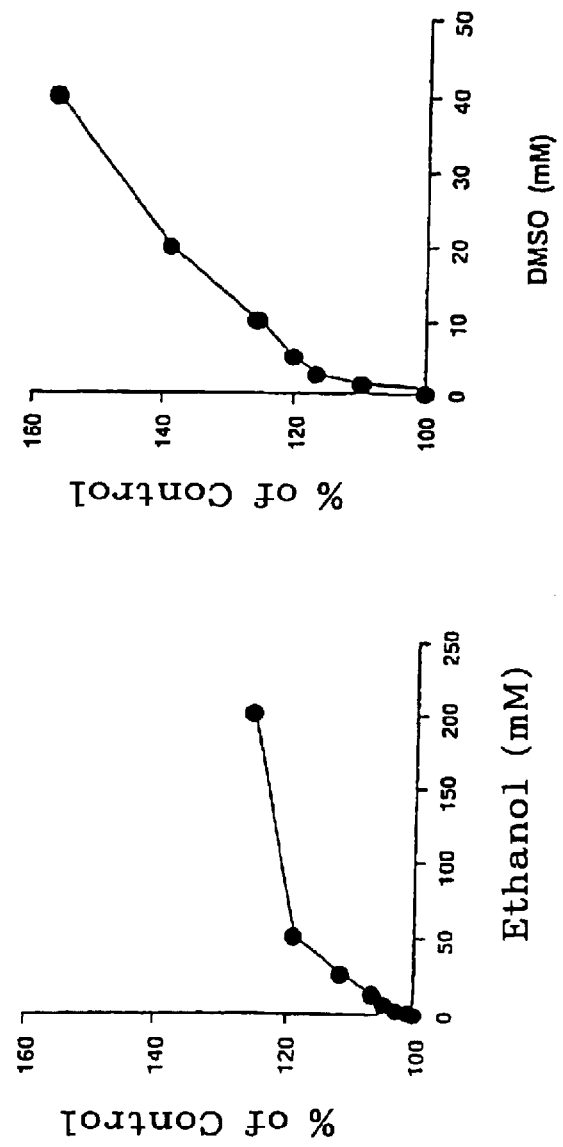
FIG. 7 shows the results of the test on the CYP2E1 activity induction shown in EXAMPLE 8.

Experimental Results (FIG. 7)

It is reported that by adding ethanol and DMSO (dimethylsulfoxide), the enzyme activity increases and intracellular CYP2E1 is induced (M. J. J. Ronis, et al., Cytochromes P450 Metabolic and Toxicological Aspects, pages 211–240, ed. by C. Ioannides et al., CRC Press, 1996). This EXAMPLE demonstrated the same results. 4-Nitrocatechol purchased from Wako Junyaku K. K. was used as the standard substance.

INDUSTRIAL APPLICABILITY

The human hepatic carcinoma-derived cultured cell lines of the present invention, which can stably express human cytochromes p450, are useful for analysis of (a) an enzyme that participates in the metabolism of xenobiotics and/or endogenous substrates, (b) a metabolic pathway of xenobiotics and/or endogenous substrates, (c) a chemical structure of the metabolite of xenobiotics and/or endogenous substrates, (d) inhibition of the metabolizing enzyme for xenobiotics and/or endogenous substrates, (e) an accelerated activity of the metabolizing enzyme for xenobiotics and/or endogenous substrates, (f) cytotoxicity by the metabolism of xenobiotics and/or endogenous substrates, (g) genotoxicity by the metabolism of xenobiotics and/or endogenous substrates, (h) carcinogenicity by the metabolism of a xenobiotic and/or endogenous substrate, (i) mutagenicity by the metabolism of xenobiotics and/or endogenous substrates, (j) hepatotoxicity by the metabolism of xenobiotics and/or endogenous substrates, or (k) xenobiotics and/or endogenous substrates that act on the liver, and for the preparation of the metabolite of xenobiotics and/or endogenous substrates.

What is claimed is:

1. An isolated cell line derived from a human hepatocarcinoma cell, which stably expresses human cytochrome P450, which is introduced by transfection, provided that when the human hepatocarcinoma cell is HepG2, the human cytochrome P450 is other than CYP2E 1, and wherein the cell line is Hepc/1A1.4, Hepc/1A2.9, Hepc/2B6.68, Hepc/2C8.46, Hepc/2C9.1, Hepc/2C19.12, Hepc/2D6.39, or Hepc/3A4.5.

* * * * *